United States Patent [19]

Jensen

[11] Patent Number: 5,141,825
[45] Date of Patent: Aug. 25, 1992

[54] METHOD OF MAKING A CERMET FUEL ELECTRODE CONTAINING AN INERT ADDITIVE

[75] Inventor: Russell R. Jensen, Lynchburg, Va.

[73] Assignee: Westinghouse Electric Corp., Pittsburgh, Pa.

[21] Appl. No.: 736,361

[22] Filed: Jul. 26, 1991

[51] Int. Cl.⁵ .............................................. H01M 8/10
[52] U.S. Cl. ................................... 429/31; 29/623.5; 427/115; 427/125; 427/126.3; 427/201; 427/203; 427/205; 427/255.3; 429/33
[58] Field of Search ................ 429/31, 33; 29/623.1, 29/623.5; 204/421; 427/115, 125, 126.1, 126.3, 201, 203, 205, 255.3

[56] References Cited

U.S. PATENT DOCUMENTS

| | | | |
|---|---|---|---|
| 3,397,968 | 8/1968 | Lavendel et al. | 75/234 X |
| 4,247,604 | 1/1981 | Marianowski et al. | 429/40 |
| 4,490,444 | 12/1984 | Isenberg | 429/31 |
| 4,582,766 | 4/1986 | Isenberg et al. | 429/30 |
| 4,597,170 | 7/1986 | Isenberg | 29/623.5 |
| 4,752,500 | 6/1988 | Donado | 427/115 |
| 4,767,518 | 8/1988 | Maskalick | 204/242 |
| 4,883,497 | 11/1989 | Claar et al. | 29/623.5 |
| 4,894,297 | 1/1990 | Singh et al. | 429/31 |
| 4,971,830 | 11/1990 | Jensen | 427/34 |

*Primary Examiner*—John Niebling
*Assistant Examiner*—William T. Leader
*Attorney, Agent, or Firm*—Daniel P. Cillo

[57] ABSTRACT

An electrode is attached to a solid electrolyte material by: (1) mixing a metallic nickel component and 1 wt% to 10 wt% of yttria stabilized zirconia having particle diameters up to 3 micrometers with an organic binder solution to form a slurry, (2) applying the slurry to a solid zirconia electrolyte material, (3) heating the slurry to drive off the organic binder and form a porous layer of metallic nickel substantially surrounded and separated by the zirconia particles, and (4) electro-chemical vapor depositing a skeletal structure between and around the metallic nickel and the zirconia particles where the metallic nickel components do not substantially sinter to each other, yet the layer remains porous.

8 Claims, 4 Drawing Sheets

METHOD OF MAKING A CERMET FUEL ELECTRODE CONTAINING AN INERT ADDITIVE

GOVERNMENT CONTRACT

The Government of the United States of America has rights in this invention pursuant to Contract No. DE-AC-21-80-ET-17089 awarded by the United States Department of Energy.

BACKGROUND OF THE INVENTION

1. Field of the Invention

The present invention relates to electrodes for solid oxide electrochemical cells and, more specifically, to improved materials for fabricating cermet electrodes on solid oxide fuel cells by electrochemical vapor deposition. In this case, electrochemical cells include fuel cells, electrolyzers and sensors that operate on the basis of electromotive force measurement and/or current measurement and which comprise a solid oxide electrolyte and attached electrodes. Solid oxide fuel cells are one typical field of application f this invention. Although this invention was developed specifically for the fabrication of electrodes on fuel cells, it may also be used to fabricate electrodes on a variety of other electrochemical devices.

2. Description of the Prior Art

Solid oxide fuel cells are high temperature electrochemical devices fabricated primarily from oxide ceramics. Typically, they contain an oxygen ion conducting solid electrolyte, such as stabilized zirconia. The electrolyte is usually a this dense film which separates two porous electrodes—an anode and a cathode. The cathode, which is maintained in an oxidizing atmosphere, is usually an oxide doped for high electrical conductivity, such as strontium doped lanthanum manganite. The anode, on the other hand, is maintained in a reducing atmosphere and is usually a cermet such as nickel-zirconia. Finally, an interconnection is usually employed which is a dense, electronically conducting oxide material which is stable in both reducing and oxidizing environments, such as doped lanthanum chromite. The interconnection is deposited on a cell as a thin gas-tight layer in such a manner that it permits the anodes and cathodes of adjacent cells to be electrically connected in series. The gas-tightness of the interconnection, in combination with that of the electrolyte, ensures that the entire cell is gas-tight, preventing mixing of the anode and cathode atmospheres.

Solid oxide cells can be operated in either an electrolysis mode or in a fuel cell mode. In an electrolysis mode, DC electrical power and steam or carbon dioxide or mixtures thereof are supplied to the cell which then decomposes the gas to form hydrogen or carbon monoxide or mixtures thereof, as well as oxygen. In the fuel cell mode, the cell operates by electrochemically oxidizing a gaseous fuel such as hydrogen, carbon monoxide, methane or other fuels to produce electricity and heat.

The use of nickel-zirconia cermet anodes for solid oxide electrolyte fuel cells is well known in the art, and taught, for example, by A. O. Isenberg in U.S. Pat. No. 4,490,444. The anode must be compatible in chemical, electrical, and physical-mechanical characteristics such as thermal expansion, to the solid oxide electrolyte to which it is attached. A. O. Isenberg, in U.S. Pat. No. 4,597,170 solved bonding and thermal expansion problems between the anode and solid oxide electrolyte, by use of a skeletal embedding growth, of for example, primarily ionically conducting zirconia doped with minor amounts of yttria. The skeletal growth extends from the electrolyte/anode interface into a porous nickel layer, with the composite structure comprising the porous cermet anode.

Anchoring of the porous nickel anode to the solid oxide electrolyte was accomplished by a modified electrochemical vapor deposition (EVD) process. While this process provided well-bonded anodes, having a good mechanical strength and thermal expansion compatibility, gas diffusion overvoltages were observed during operation, lowering overall cell performance.

In order to reduce gas diffusion overvoltages, A. O. Isenberg et al., in U.S. Pat. No. 4,582,766, taught oxidizing the nickel in the cermet electrode to form a metal oxide layer between the metal, and the electrolyte, the embedding skeletal member. Subsequent reduction of the metal oxide layer forms a porous metal layer between the metal, and the electrolyte and skeletal member allowing greater electrochemical activity.

U.S Pat. No. 4,894,297 (Singh et al.), taught impregnating the cermet fuel electrode with chemicals that form metal oxides upon heating, for example Mg, Ca+Al, Sr+Al, Zr, Y and Ce salts, in order to prevent carbon deposition from hydrocarbon fuel. Further improvements were made in U.S. Pat. No. 4,767,518 (Maskalick) which taught discrete deposits of praseodymium oxide, dysprosium oxide and terbium oxide, present in the range of from 0.1 wt % to 5 wt % in the cermet electrode, to reduce cell over-potential and increase cell efficiency.

While it has been established that fuel cell anodes fabricated by the EVD process provide fuel cells with acceptable performance, one aspect of the EVD process can be problematical. Specifically, the EVD process is performed by applying a nickel powder layer on the electrolyte of a cell, using an aqueous powder slurry containing an organic binder. After drying, the cell is then heated to the EVD operating temperature. During heating, the nickel powder layer sinters, thereby consolidating the nickel powder into a porous body. Some degree of sintering is required to develop adequate electrode mechanical strength and electrical conductivity. Once the operating temperature is reached, EVD is performed and zirconia is deposited throughout the electrode. This zirconia then effectively prevents any further sintering of the electrode.

Occasionally, problems with electrode peeling and/or splitting during heating to the EVD operation temperature have been encountered. Electrode peeling and splitting are both the result of stresses produced in the electrode during sintering. Such stresses occur because the sintering of the electrode is constrained by the fuel cell on which it is applied. If it were free-standing, the electrode would shrink continuously as it sintered. Because the shrinkage of the electrode is inhibited by being applied to an essentially non-sintering substrate, surface tractions develop at the interface between the electrode and the electrolyte. These tractions are balanced by stresses induced in the electrode layer.

The stresses in the electrode give rise to a peeling force at electrode edges and tensile stresses within the bulk of the electrode layer. The latter stresses can exceed electrode strength and cause splitting of the electrode. While a certain degree of sintering is essential to develop required electrode mechanical and electrical properties, the occurrence of electrode peeling and splitting indicates that an excessive amount of electrode sintering can occur. What is needed is a method for controlling the degree of sintering of the electrode during heating to the EVD operation temperature. A main objective of this invention is to provide such a method.

SUMMARY OF THE INVENTION

Accordingly, the present invention resides in a method of applying an adherent, conductive, porous electrode, characterized by the steps:

(1) mixing a metallic nickel powder component selected from the group consisting of equiaxed particles, filamentary particles, and mixtures thereof, yttria stabilized zirconia particles having diameters up to 3 micrometers where the zirconia particles are smaller than the metallic nickel and constitute from 1 wt % to 10 wt % of the nickel-zirconia mixture, and an organic binder solution, to form a homogeneously dispersed slurry;

(2) applying the slurry to the surface of dense stabilized zirconia solid electrolyte material;

(3) heating the slurry to drive off the binder and form porous a layer of metallic nickel substantially surrounded and separated by smaller yttria stabilized zirconia particles;

(4) electrochemical vapor depositing, at a temperature of from 1000° C. to 1400° C., a dense yttria stabilized zirconia skeletal structure which forms between and around the metallic nickel and the yttria stabilized zirconia particles, where the zirconia particles get embedded into the skeletal structure as it grows thicker with time, to form a conducting layer where metallic nickel particles are separated and do not substantially sinter to each other yet the layer remains porous, to provide an electrode intimately attached to the solid electrolyte material.

The present invention resides in a modification in the material used to fabricate fuel cell anodes by electrochemical vapor deposition (EVD). The term "electrochemical vapor deposition," as used herein, refers to a process by which dense oxide films (or in the present case, of anode fabrication skeletal growths) can be fabricated on electrochemical devices. Specifically, the process is performed at elevated temperature where a metal halide vapor is applied at low oxygen partial pressure to one surface of a dense electrolyte film. On the opposing surface of the electrolyte is applied a gaseous source of oxygen at high oxygen partial pressure. The oxygen partial pressure gradient across the electrolyte film causes an oxygen ion flux to flow from the high to the low oxygen partial pressure surface. At the low oxygen partial pressure side, the oxygen ions react with the halide vapors to form a substantially 100% dense oxide. In the present case of anode fabrication by EVD, the metal halides include, but are not limited to, zirconium and yttrium halide. Yttrium halide is included to dope the zirconia grown so that it is stabilized in the cubic structure. The doped zirconia grown in this process grows as a dense film over the surfaces of the sintered nickel particles in the electrode in a structure resembling a three-dimensional skeleton.

In the present EVD fuel cell anode fabrication process, a slurry comprising nickel metal powder and an aqueous solution of an organic binder is employed. The nickel powder possesses a roughly equiaxed particle shape, that is, roughly spherical, and an average particle size in the range of 3 μm to 7 μm. An example of such a powder which is commercially available is INCO Type 123 nickel powder. The organic binder is included in the slurry to consolidate the nickel powder in the dried electrode prior to processing. The binder is fugitive in the sense that it is driven from the electrode during heating to the EVD operation temperature. An example of such a binder is polyvinyl alcohol.

The present invention pertains to modifications made to the nickel slurry to control the sintering behavior of electrodes deposited from this material. The primary modification is the introduction of a small amount of a fine particle size oxide material. Such oxides have been found to be extremely effective in reducing the amount of sintering induced shrinkage of nickel fuel electrode materials. When such oxides are added to the nickel slurries at contents of up to 10 wt % (of total nickel and oxide weight), the sintering induced shrinkage of such electrode material under simulated EVD heating conditions can be varied from that which occurs with no oxide addition to almost no shrinkage at the higher oxide contents. In other words, the amount of sintering induced shrinkage during EVD heating can be designed into an electrode material by the addition of a relatively small amount of oxide particles. As discussed below, all oxide materials are not suitable, as many are not stable in the EVD metal halide atmosphere. Yttria stabilized zirconia has been identified as being a suitable oxide species.

Another modification in the material used in EVD fabrication of fuel cell anodes which has been investigated and shown to be beneficial is changing the morphology of the nickel powder particles used in the nickel slurry. As mentioned, in the current EVD. anode fabrication process, nickel powder with a roughly equiaxed particle shape is employed. Other forms of nickel powder can be used, however. One type of powder which has desirable properties, which are discussed below, is so-called filamentary nickel powder. Particles of this type powder are aggregates of small, roughly equiaxed particles, of the order of one to two micrometers in size. These small particles are aggregated into elongated structures resembling beads on a string. This analogy is only approximate, however, as the particles also exhibit branching and clusters of particles within the particle chains. One example of a filamentary type nickel powder which is commercially available is INCO Type 287 nickel powder.

An important result of the high degree of structure possessed by a filamentary nickel powder is that nickel powder layers fabricated from this powder using slurry application techniques are extremely porous. The structure of the powder particles prevents efficient packing of the particles during drying of the slurry. After sintering, electrodes fabricated using filamentary powders retain a high degree of porosity so that, when compared at constant electrical conductivity, filamentary powder electrodes are more porous than electrodes sintered from equiaxed-type nickel powders. The retention of a high degree of porosity in a fuel cell anode is important because it reduces diffusional polarization losses and consequently increases cell performance.

BRIEF DESCRIPTION OF THE DRAWINGS

In order that the invention can be more clearly understood, conventional embodiments thereof will now be described, by way of example, with reference to the accompanying drawings in which.

DESCRIPTION OF THE PREFERRED EMBODIMENTS

In the preferred embodiment, the porous electrode will be applied on a tubular solid electrolyte, supported by a tubular air electrode structure, to provide a tubular fuel cell, where an optional support tube for the air electrode can also be included.

Figure 1:
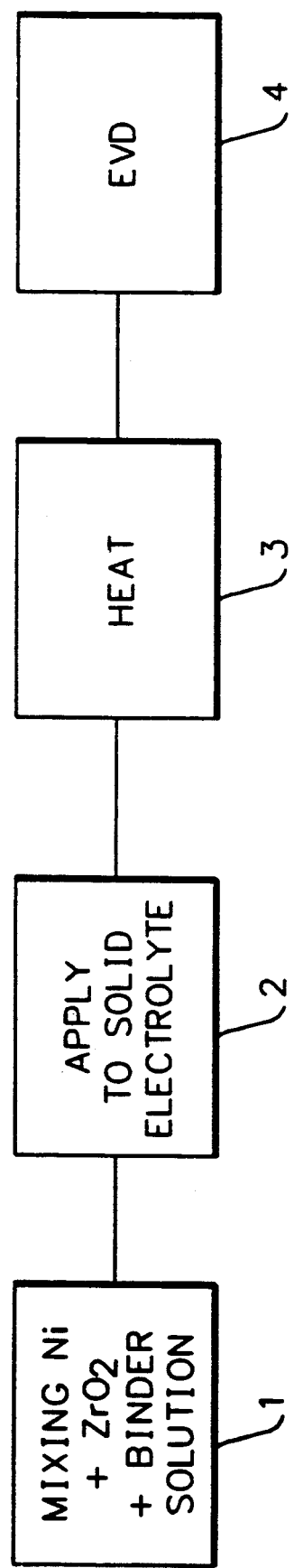
FIG. 1 is a block diagram of the method of this invention.

In this invention, metallic nickel, yttria stabilized zirconia particles, and a fugitive liquid containing a binder are mixed together to form a homogeneously dispersed slurry (step 1 of FIG. 1). The zirconia particles will constitute from 1 wt % to 10 wt %, preferably from 1 wt % to 7 wt % of the nickel-zirconia mixture. Under 1 wt % zirconia, too few zirconia particles are present to effect substantially the sintering of the metallic nickel particles, leading to increased linear shrinkage and loss of porosity. Over 10 wt % zirconia, no further positive results in terms of increased porosity or decreased linear shrinkage result and electrical conductivity decreases.

The yttria stabilized zirconia particles are preferably $(ZrO_2)_{0.9}(Y_2O_3)_{90.1}$, and will have a particle size range at initial mixing of up to 3 micrometers, most preferably from 0.25 micrometer to 3 micrometers. Zirconia particles with an average particle size significantly greater than 3 micrometers are not preferred because they are much less effective in controlling the sintering of the nickel particles and such particles must be added in much higher amounts to attain a given degree of nickel sintering resistance.

This yttria stabilized zirconia additive, unlike other materials such as powdered graphite, char forming cellulose, chromium oxide and cerium oxide can resist not only electrochemical vapor deposition temperatures in the range of 1000° C. to 1400° C., but also long-term operation in a fuel cell generator at 1000° C. to 1100° C. Other oxides, such as $Cr_2O_3$, $CeO_2$, and $La_{0.84}Sr_{0.16}CrO_3$ have been found to be stable at long-term generator operation temperatures but are volatilized from of the electrode during electrochemical vapor deposition. This volatilization occurs by a displacement reaction where the metal chlorides used in the EVD process react with the oxides. Metallic chlorides formed from the metallic constituent of the oxides are liberated, leaving discrete particles of EVD-grown zirconia in their place. This type reaction interferes with the deposition process and reduces the strength of the electrode to electrolyte bond.

The metallic nickel powder component can be of an equiaxed nickel particle type, where the particles have roughly spherical diameters from 3 micrometers to 7 micrometers, such as INCO Type 123 nickel powder. Preferably, the nickel powder component will be of a filamentary structure, such as INCO Type 287 nickel powder, where the individual particles are aggregates of smaller particles attached to form a bead or chain-like structure. The diameter of the small particles in the filamentary particle is of the order of one to two micrometers. The overall size of the filamentary particles is variable, due to a wide variation in chain length and degree of branching. The filamentary powder generally provides higher porosity but higher linear shrinkage than equiaxed nickel powder.

Most preferably, when equiaxed particle-type nickel powder is used, the most effective range of stabilized zirconia addition is in the range of from 1 wt % to 6 wt % of the nickel-zirconia mixture; when filamentary nickel powder is used, the most effective range of stabilized zirconia addition is in the range of from 2.5 wt % to 8 wt %.

Useful aqueous binders in the nickel slurry could include polyvinyl alcohol, methyl cellulose, and the like, as long as it will evaporate or burn out of the electrode without leaving harmful residues during heating (step 3 in FIG. 1) after application of the slurry (step 2 in FIG. 1) to the solid electrolyte material. After the binder is removed from the electrode, the metallic nickel is substantially surrounded by smaller yttria stabilized zirconia particles.

Electrochemical vapor deposition (step 4 in FIG. 1) is accomplished as previously described, and as described in more detail in U.S. Pat. No. 4,597,170, herein incorporated by reference. In general, the material that binds the conductor particles to the electrolyte is formed by the electrochemical oxidation of metal halides. The binding material is preferably selected to be the same material as the electrolyte (or the same material modified by doping) so that a bond forms between the binding material and the electrolyte and there is minimal thermal expansion mismatch between the two materials. The electrochemical vapor deposition is performed at elevated temperature where the metal halides are delivered to the exterior of a cell in gaseous form. Oxygen ions diffuse through the electrolyte and react with the halides. Chlorides are preferred as they are inexpensive and have acceptable vapor pressures. The reaction produces a metal oxide binding material by, for example, reaction of zirconium chloride with oxygen. If the binding material is to be stabilized zirconia, it is necessary to use a mixture of a zirconium halide and a halide of the stabilizing element as the second reactant. The proportion of the two halides in the mixture is selected to produce the desired composition of the binding material.

The minimum temperature at which electrochemical vapor deposition may be performed is, in this case governed by the constraint that the electrolyte must have a relatively high oxygen ion conductivity. The maximum temperature is dictated by the requirement that the process not damage the cell. Accordingly, the temperature of this process is preferably in the range of about 1000° C. to about 1400° C. Typically, about 1 to about 30 minutes is required to produce sufficient binding material to adequately bond the conductor particles to the electrolyte. The reaction proceeds faster at higher temperatures and is terminated when the desired amount of binder material is deposited. High densities should be avoided for fuel electrodes, as fuel electrodes must still be permeable to the gases used in operating a fuel cell.

The invention will now be illustrated with reference to the following Example, which is not be considered limiting in any way.

EXAMPLE

A variety of metallic nickel-yttria stabilized zirconia-polyvinyl alcohol binder slurries were prepared. Samples for sintering experiments were prepared by tape-casting the slurries into sheets with thicknesses comparable to that obtained for slurry coatings applied to fuel cells. The sheets were then diced to give rectangular samples for sintering. The slurries were not applied to fuel cells or any other substrate to avoid the possibility that the sintering of the slurry layer would be constrained by the substrate. Rather, the samples were sintered by placing them on polished alumina plates, on which they were able to sinter with essentially no constraints. No evidence was found in any test that the samples developed any adhesion to the alumina. The sintering had to be performed with the samples completely unconstrained so that the effect of slurry additives in sintering would not be confounded by that due to substrate constraints.

In all cases, the stabilized zirconia added to the slurries was $(ZrO_2)_{0.9}(Y_2O_3)_{0.1}$ at an approximate particle size of 0.5 micrometer. The two types of metallic nickel components used were the INCO Type 123 nickel powder and INCO Type 287 nickel powder, both heretofore described. Slurries were made with no stabilized zirconia (control sample) and from 0.6 wt % to 6.1 wt % stabilized zirconia based on nickel plus zirconia weight.

Figure 2:
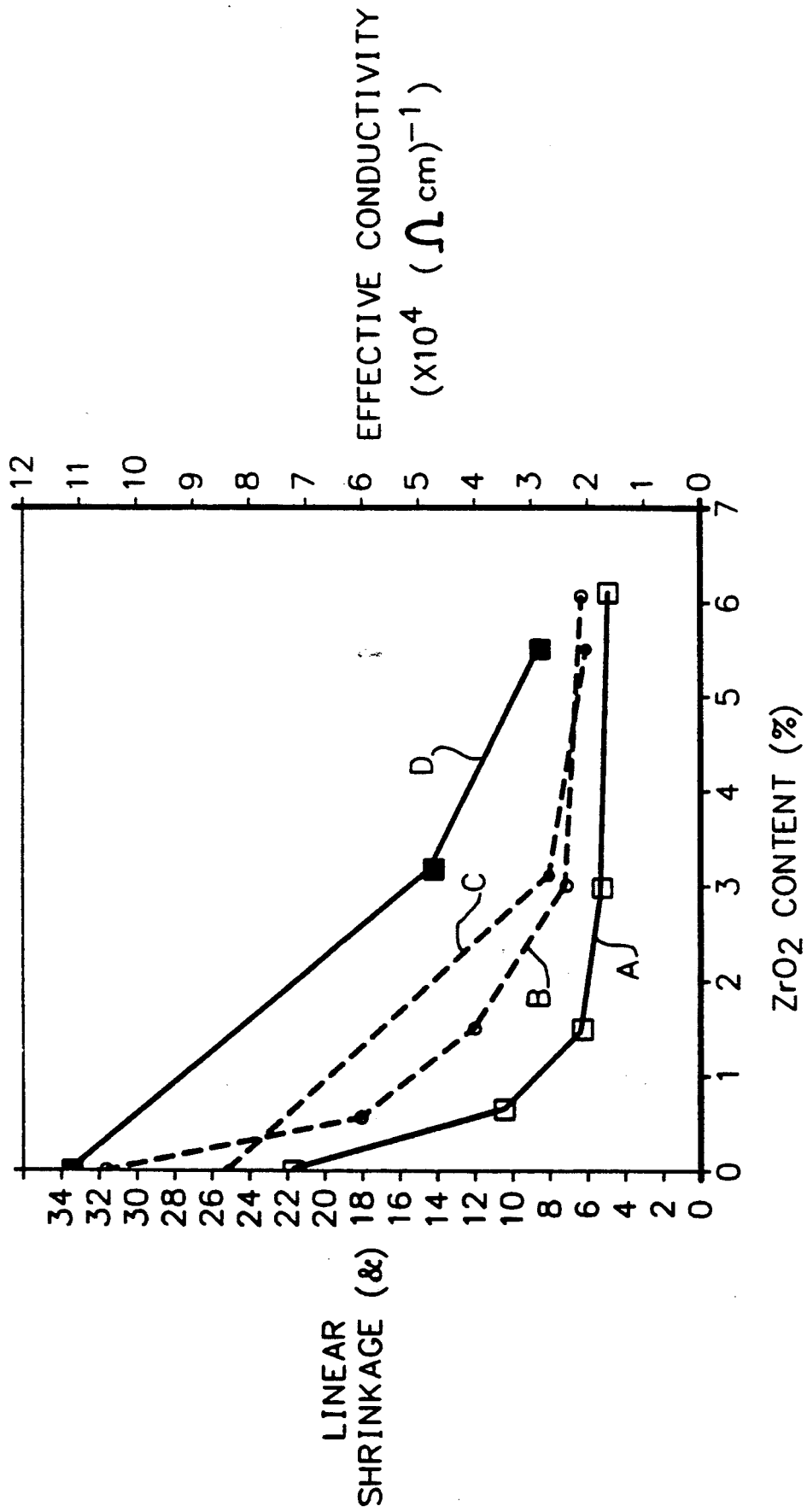
FIG. 2 is a graph of fuel electrode linear shrinkage and conductivity versus stabilized zirconia content for equiaxed and filamentary nickel powder.
Figure 3:
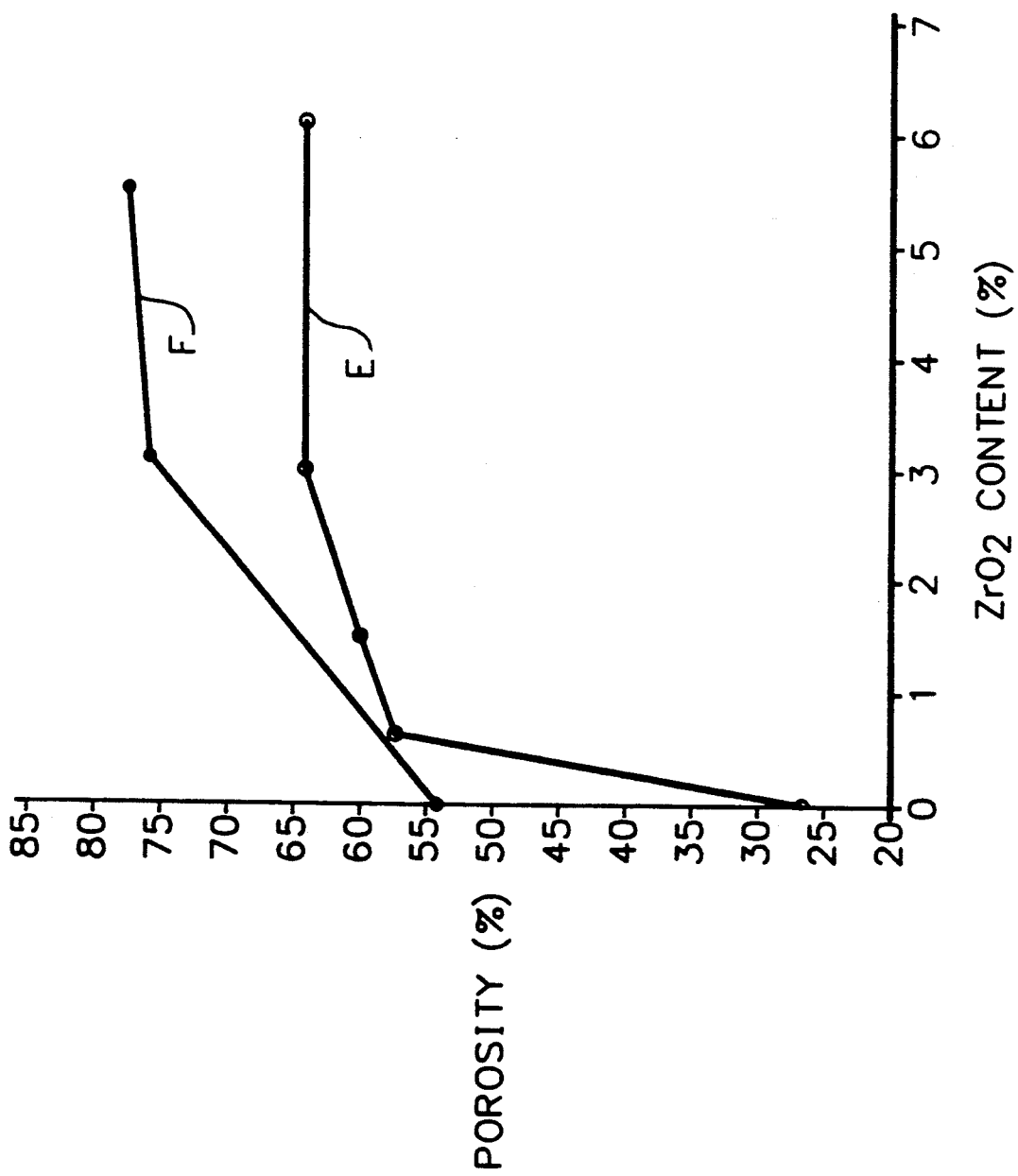
FIG. 3 is a graph of fuel electrode porosity versus stabilized zirconia content for equiaxed and filamentary nickel powder.
Figure 4:
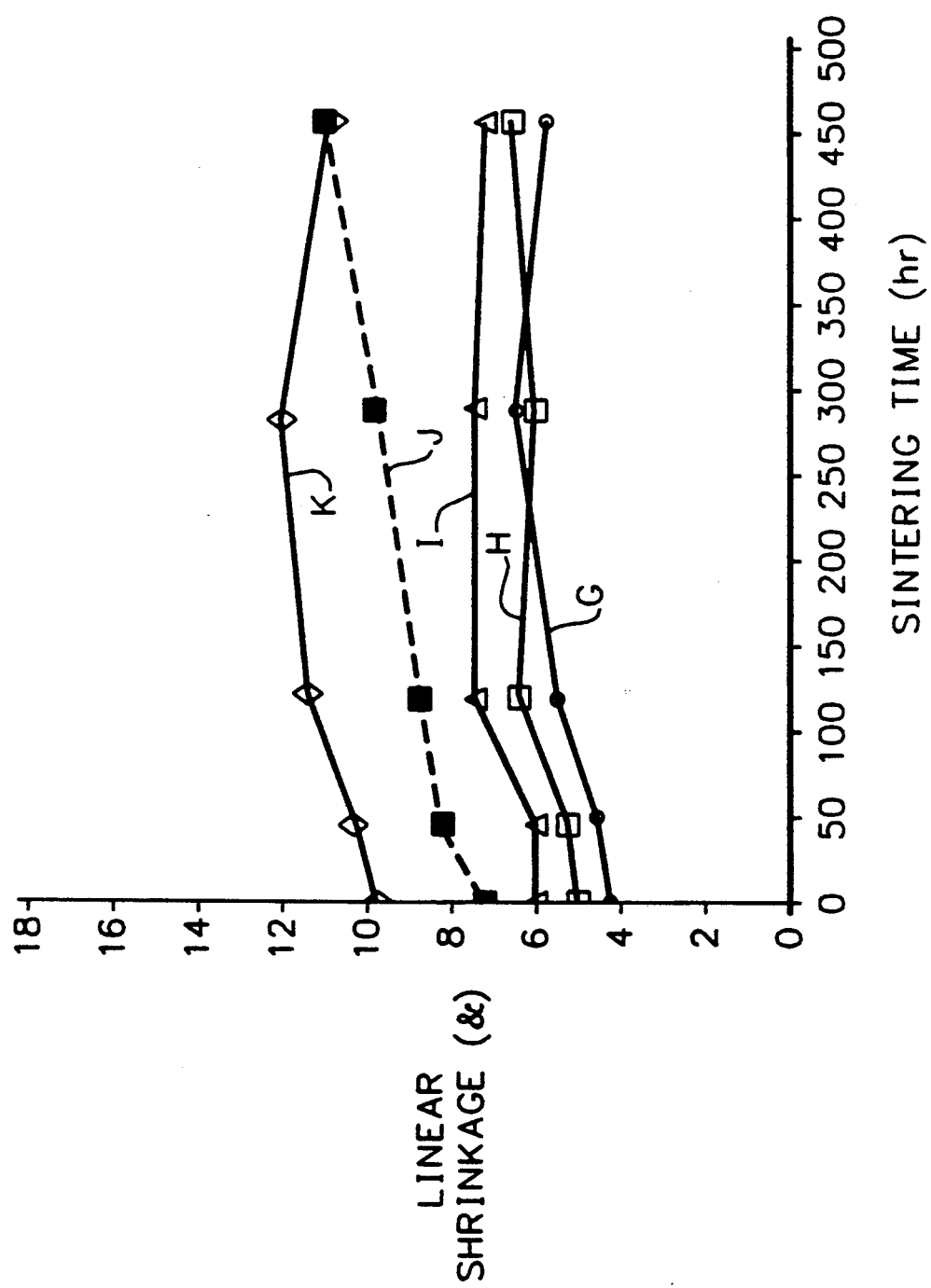
FIG. 4 is a graph of fuel electrode linear shrinkage versus long-term fuel electrode sintering for equiaxed and filamentary nickel powder.

After tape-casting, the slurries were allowed to dry in air and then diced into specimens. The polyvinyl alcohol was driven off during heating to the sintering temperature, so that the stabilized zirconia (in all but the control sample) in various degrees, substantially surrounded most of the metallic nickel. The resulting nickel-zirconia films were from 200 micrometers to 500 micrometers thick. The samples were cross-sectioned, polished and mounted, so that scanning electron microscopy of the various layers could be performed. Values for linear shrinkage, effective electrical conductivity, and porosity versus stabilized zirconia content were determined. Shrinkage and porosity were determined using dimensional measurements. Electrical conductivity was determined using standard four-point probe sheet resistance measurements. Additionally, long-term sintering tests were conducted for up to 500 hours. The results of these tests are shown in the graphs of FIGS. 2, 3, and 4. There was no EVD growth of a zirconia skeleton for these tests.

In FIG. 2 the left vertical axis represents linear shrinkage of the Ni-zirconia electrode and the right vertical axis represents effective electrical conductivity of the nickel-zironia electrode at ambient temperature in units of $\times 10^4 (\Omega cm)^{-1}$ for various yttria stabilized zirconia particle additions. These measurements were made after the samples had been sintered in 96% $N_2$ + 4% $H_2$ in a furnace, at a temperature increase of 5.5° C./min to a maximum temperature of 1300° C., followed by furnace cooling. This simulates the temperature-time profile used in the EVD process.

In FIG. 2, the open squares, curve A, indicate Type 123 nickel powder based electrode shrinkage. The open circles, curve B, indicate Type 123 equiaxed nickel powder based electrode conductivity. The darkened circles, curve C, indicate Type 287 filamentary nickel powder based electrode conductivity; the darkened squares, curve D, indicate Type 287 nickel powder based electrode shrinkage. As can be seen, the best combination of values for all the samples would appear to be at approximately 3 wt % yttria stabilized zirconia content, to provide good linear shrinkage control yet reasonable electrical conductivity values. Because there is an obvious trade-off between sintering shrinkage control and electrical conductivity, the precise value to be used for the zirconia addition has to be determined by cell performance requirements.

In FIG. 3, the left vertical axis represents porosity (0% porosity = theoretical density) of the nickel-zirconia electrode for various yttria stabilized zirconia particle additions, after the samples were sintered in 96% $N_2$ + 4% $H_2$ in a furnace, at a temperature increase of 5.5° C/min to a maximum temperature of 1300° C. and furnace cooled. The open circles, curve E, indicate Type 123 equiaxed nickel powder based fuel electrode porosity, and the darkened circles, curve F, indicate Type 287 filamentary nickel powder based electrode porosity. As can be seen, the filamentary Type 287 nickel powder provides a more porous structure.

FIG. 4 provides data on long-term sintering behavior during high temperature exposure in a simulated fuel cell generator environment. In FIG. 4, the left vertical axis represents linear shrinkage and the horizontal axis represents sintering time in hours, at 1100° C. in 96% $N_2$ and 4% $H_2$. Initial sintering was in 96% $N_2$ + 4% $H_2$ at a temperature increase of 5.5° C./min to a maximum temperature of 1300° C. In this experiment:

Curve G = Type 123 equiaxed nickel powder at 6.1 wt. % yttria stabilized zirconia particles.
Curve H = Type 123 equiaxed nickel powder at 3.0 wt. % yttria stabilized zirconia particles.
Curve I = Type 123 equiaxed nickel powder at 1.5 wt. % yttria stabilized zirconia particles.
Curve J = Type 287 filamentary nickel powder at 5.5 wt. % yttria stabilized zirconia particles (darkened squares).
Curve K = Type 123 equiaxed nickel powder at 0.6 wt. % yttria stabilized zirconia additive particles.

As can be seen, electrode material based on the equiaxed particle nickel, Type 123, with over about 1 wt % yttria stabilized zirconia particles shows almost no further shrinkage with time. The filamentary particle nickel, Type 287, with 5.5 wt % yttria stabilized zirconia does, however, show some continued shrinkage. While it would be an important added benefit, the main purpose of the addition of the zirconia to the fuel electrode material is not to completely inhibit further sintering of the fuel electrode during long-term operation.

Zirconia is added primarily to facilitate electrode fabrication. The zirconia skeleton formed in the electrode during the EVD operation is the major source of electrode sintering resistance. Nevertheless, a linear shrinkage of about 11% after pre-sintering plus 460 hours at 1100° C. (filamentary particle nickel—curve J) is still far superior to the 33% linear shrinkage obtained with no particulate zirconia additive after only presintering (filamentary particle nickel—curve D in FIG. 2 at $ZrO_2$ content = 0%).

In several instances, fuel cells were fabricated using nickel-zirconia slurries in the fuel electrode electrochemical vapor deposition process. Here, the zirconia particles became embedded into the skeletal structure and remained in particulate form. After electrode fabrication, these particles also help prevent particle-to-particle nickel sintering and provide porous fuel electrodes. These completed fuel cells, using INCO Type 123 equiaxed particulate nickel and 3 wt % $(ZrO_2)_{0.9}(Y_2O_3)_{0.1}$ powder additive prior to EVD, were tested and provided high performance fuel cells.

I claim:

1. A method of applying an adherent, conductive, porous electrode, comprising the steps:

(1) mixing a metallic nickel powder component selected from the group consisting of equiaxed particles, filamentary particles, and mixtures thereof, yttria stabilized zirconia particles having diameters up to 3 micrometers where the zirconia particles are smaller than the metallic nickel and constitute from 1 wt % to 10 wt % of the nickel-zirconia mixture, and an organic binder solution, to form a homogeneously dispersed slurry;

(2) applying the slurry to the surface of dense stabilized zirconia solid electrolyte material;

(3) heating the dried slurry to drive off the binder and form a porous layer of metallic nickel substantially surrounded and separated by smaller yttria stabilized zirconia particles;

(4) electrochemical vapor depositing, at a temperature of from 1000° C. to 1400° C., a dense yttria stabilized zirconia skeletal structure which forms between and around the metallic nickel and the yttria stabilized zirconia particles, where the zirconia particles get embedded into the skeletal structure as it grows thicker with time, to form a conducting layer where metallic nickel particles are separated and do not substantially sinter to each other yet the layer remains porous, to provide an electrode intimately attached to the solid electrolyte material.

2. The method of claim 1, where the electrolyte is disposed on a tubular, ceramic air electrode comprising lanthanum manganite, to provide a tubular fuel cell.

3. The method of claim 1, where the yttria stabilized zirconia particles are $(ZrO_2)_{0.9}(Y_2O_3)_{0.1}$.

4. The method of claim 1, where the zirconia particles constitute from 1 wt % to 7 wt % of the nickel-zirconia mixture and have a particle size range at addition to the mixture of from 0.25 micrometer to 3 micrometers.

5. The method of claim 1, where the metallic nickel is a mixture of equiaxed and filamentary nickel powder.

6. The method of claim 1, where the metallic nickel powder is an equiaxed form and the zirconia particles constitute up to 6 wt % of the nickel-zirconia mixture.

7. The method of claim 1, where the metallic nickel powder is a filamentary form and the zirconia particles constitute up to 8 wt % of the nickel-zirconia mixture.

8. A fuel cell made by the method of claim 2.

* * * * *